US 6,537,323 B2
Mar. 25, 2003

(12) United States Patent
Weinstein et al.

(54) LOW PROFILE CARDIAC STABILIZATION DEVICE AND METHOD OF USE THEREFORE

(75) Inventors: Martin J. Weinstein, South Dartmouth, MA (US); Quinton Farrar, Assonet, MA (US)

(73) Assignee: Genzyme Corporation, Cambridge, MA (US)

( * ) Notice: Subject to any disclaimer, the term of this patent is extended or adjusted under 35 U.S.C. 154(b) by 182 days.

(21) Appl. No.: 09/770,692

(22) Filed: Jan. 26, 2001

(65) Prior Publication Data
US 2001/0037054 A1 Nov. 1, 2001

Related U.S. Application Data

(63) Continuation-in-part of application No. 09/561,415, filed on Apr. 28, 2000, now Pat. No. 6,478,733.

(51) Int. Cl.[7] .................................................. A61B 1/32
(52) U.S. Cl. .................... 623/213; 600/228; 600/232
(58) Field of Search ........................... 600/201, 213, 600/214, 215, 219, 222, 227, 231, 233, 37, 232, 228

(56) References Cited

U.S. PATENT DOCUMENTS

| 2,590,527 A | 3/1952 | Fluck |
| 4,688,570 A | 8/1987 | Kramer et al. |
| 4,702,230 A | 10/1987 | Pelta |
| 5,167,223 A | 12/1992 | Koros et al. |
| 5,231,974 A | 8/1993 | Giglio et al. |
| 5,503,617 A | 4/1996 | Jako |
| 5,509,890 A | 4/1996 | Kazama |
| 5,727,569 A | 3/1998 | Benetti et al. |
| 5,730,757 A | 3/1998 | Benetti et al. |
| 5,749,892 A | 5/1998 | Vierra et al. |
| 5,782,746 A | 7/1998 | Wright |
| 5,799,661 A | 9/1998 | Boyd et al. |
| 5,836,311 A | 11/1998 | Borst et al. |
| 5,865,730 A | 2/1999 | Fox et al. |
| 5,876,332 A | 3/1999 | Looney |
| 5,882,299 A | 3/1999 | Rastegar et al. |
| 5,885,271 A | 3/1999 | Hamilton et al. |
| 5,947,896 A | 9/1999 | Sherts et al. |
| 5,957,835 A | 9/1999 | Anderson et al. |
| 5,976,080 A | 11/1999 | Farascioni |
| 6,019,722 A | 2/2000 | Spence et al. |
| D421,803 S | 3/2000 | Koros et al. |
| 6,050,266 A | 4/2000 | Benetti et al. |
| 6,071,295 A | 6/2000 | Takahashi |
| 6,102,854 A | 8/2000 | Cartier et al. |

FOREIGN PATENT DOCUMENTS

| EP | 0 791 330 A2 | 8/1997 |
| EP | 0 820 721 A1 | 1/1998 |
| EP | 0 993 806 A2 | 4/2000 |
| WO | WO 97/10753 | 3/1997 |
| WO | WO 97/26828 | 7/1997 |
| WO | WO 98/48703 | 11/1998 |
| WO | WO 98/48704 | 11/1998 |
| WO | WO 98/49947 | 11/1998 |
| WO | WO 99/08585 | 2/1999 |
| WO | WO 99/16367 | 4/1999 |
| WO | WO 00/10466 | 3/2000 |

*Primary Examiner*—Cary E. O'Connor
(74) *Attorney, Agent, or Firm*—Richard D. Allison; Thomas J. DesRosier

(57) ABSTRACT

The present invention relates to a low profile stabilizer that immobilizes tissue at a surgical site wherein the device includes a stabilizer having a base portion with elongate extending members that surround the sides of an aperture area and a removable end portion which is removable from the base portion and which surrounds the remaining side of the aperture area and wherein the stabilizer is preferably used in combination with a pair of flexible connectors that are threaded through the tissue adjacent to the aperture area to draw the tissue into contact with the aperture area of stabilizer and into contact with a pair of tab members extending from the bottom surface of the stabilizer such that the flow of blood through a blood vessel is occluded by tab members when the flexible connectors are releasably attached to the stabilizer.

30 Claims, 7 Drawing Sheets

LOW PROFILE CARDIAC STABILIZATION DEVICE AND METHOD OF USE THEREFORE

The present application is a continuation in part of U.S. Ser. No. 09/561,415 filed on Apr. 28, 2000, now U.S. Pat. No. 8,478,733, which is related to U.S. Ser. No. 09/410,982 filed Oct. 1, 1999, now U.S. Pat No. 6,458,079, which is a continuation-in-part of U.S. Ser. No. 09/307,195, pending, filed on May 7, 1999 which is a continuation application of International Application No. PCT/US98/08348, filed on Apr. 24, 1998 and designating the United States which is a continuation-in-part application of U.S. Ser. No. 08/845,333, now U.S. Pat. No. 6,033,362, filed on Apr. 25, 1997, the entire teachings of the above application being incorporated herein by reference.

BACKGROUND OF THE INVENTION

Numerous devices have been used to position tissue at a surgical site to aid in the performing of surgical procedures. Various retractors or similar devices, have been used for many years to hold an artery in position during operations adjacent to the heart to prevent movement of the artery. This serves to minimize the risk of injury to the artery and adjacent tissue and can facilitate the creation of the desired anastomosis.

A recently developed procedure, referred to as the minimally invasive direct coronary artery bypass procedure, has been used to graft onto a coronary artery without cardiopulmonary bypass. This procedure involves the grafting of the left internal mammary artery (LIMA) or saphenous vein onto the left anterior descending (LAD) or other coronary artery. As this procedure does not require the use of a heart lung machine to oxygenate and pump blood, the morbidity and mortality associated with this procedure is substantially lower than previous bypass techniques. A problem associated with the less invasive procedures, however, is that while the heart continues to pump during the procedure, the motion of the heart can interfere with the surgeon's task of attaching the LIMA or saphenous vein to the LAD. There is also a need to stop blood flow in the area of the graft to maintain a clear field of view and provide precise suture placement.

Two basic strategies have been employed to address the problem of operating on a moving site, one being the use of pharmacological agents to limit heart motion. The use of pharmacological agents is undesirable and may impair circulatory function. The other approach to stabilization is mechanical, such as a two prong retractor that is pushed down against the heart on both sides of the artery, or alternatively, upward traction away from the moving heart by suction, traction tape or suture thread. Both of the mechanical options, however, have problems associated with them. Traction by compression of the heart requires an increased amount of downward force on the tissue of the heart along a relatively large surface area. Although this type of device does serve to immobilize the tissue at the surgical site, it may also compromise the ability of the heart to maintain circulation and result in hypotension. Upward traction through the use of suction requires that the entire surface of the device be in contact with the tissue of the heart along a relatively large surface area to maintain suction. As with the compression type of devices, the suction type of device may cause injury, stenosis or occlusion of the vessel when upward traction that is sufficient to immobilize the tissue along the surgical site is used. Additionally, because various surfaces of the heart need to be accessed, it is not always possible or convenient to apply compression or upward traction to the desired surface of the heart.

There is a continuing need for improvement in devices and methods for retaining tissue at surgical sites to further reduce the risks associated with surgical procedures where the devices and methods are inexpensive, versatile, safe and reliable. The increased use of the above-described mechanical devices have also illustrated the need for a device that provides the desired local stabilization while allowing the surgeon to quickly set up and remove the stabilizing device while also providing access to multiple locations and surfaces on the heart of the patient.

SUMMARY OF THE INVENTION

The present invention relates to a cardiac stabilizer for immobilizing tissue at a surgical site and to a method of using the stabilizer during a surgical procedure. A preferred embodiment of the stabilizer includes a generally oblong, ovoid or elongate retaining element, platform or stabilizer having an aperture area that exposes the surgical site and a plurality of tape holders that are used to capture the tissue adjacent to the aperture area relative to the stabilizer. A handle can be attached to or fabricated with the stabilizer so that the user can manipulate the position of the stabilizer as needed. As used herein, the stabilizer generally refers to a device that is movable into a contacting relationship with the tissue of a patient to reduce the movement of the tissue at the desired surgical site.

The coronary arteries are typically about 1–2 mm in diameter, and the pumping heart can move these arteries over distances of several millimeters during each heartbeat. Because the movement of even 1 or 2 millimeters can result in a displacement of the grafting site that can substantially interfere with suturing an effective anastomosis, it is desirable to restrain movement of the artery at the surgical site in any direction to less than about 1 mm. The stabilizer and tapes of the present invention preferably restrain movement of the tissue relative to the stabilizer.

A preferred embodiment of the invention comprises a low profile retaining element or stabilizer that includes a removable end piece that is removable to form an open ended aperture area to permit removal of the stabilizer from around the grafted artery following the procedure. The end piece is used to contribute to the stability of the stabilizer during the procedure and then is readily removable to allow for the passage of the grafted vessel therethrough. Additionally, the end piece includes a pair of tape holders thereon to assist in the capture of the tissue adjacent to the aperture area. Therefore, the stabilizer can be separated prior to the removal of the tapes so that the proximal portion of the stabilizer may be remove from the surgical site prior to the removal of the end piece. The present invention is beneficial in any procedure where it is desirable to stabilize tissue at a surgical site. For example, the stabilizer can also be used for grafting vessels onto the diagonal, right or other coronary arteries without altering the heart's pumping function or during surgery on various other organs or tissues.

In a preferred embodiment of the invention, a handle or articulating arm may be secured to the platform of the stabilizer and may be held in position by the user, attached to various locations on a retractor frame that is fixed around the operative site or simply clipped to a drape around the site.

In yet another preferred embodiment of the present invention, the stabilizer includes a generally oblong or elongate shape wherein the lengthwise dimension of the stabilizer is greater than the width dimension. In this form of the invention, the connector for attachment to a handle or other member is located on the stabilizer generally along the an end portion of the stabilizer such that the application of force along the handle is applied over the blood vessel that is to be operated on and near the aperture area. Therefore, this arrangement takes up less surface area on the heart of the patient while providing sufficient leverage to provide a stable surgical site through the aperture area.

In a further preferred embodiment, the stabilizer has tape holder elements disposed in the longitudinal dimension and/or along the periphery of the stabilizer. Each holder element includes one or more slots that frictionally grip an end of a connector such as elastic tape or thread that extends through the tissue of the patient to connect the tissue to the stabilizer. The use of slots or grooves on the surface of the stabilizer allows the user to place the connectors such as elastic tape or thread around the outer or inner surface of the stabilizer to position tissue at the surgical site within the stabilizer aperture and to minimize movement of the tissue relative to the stabilizer during the procedure. When these slots are used, the tapes are threaded through the tissue of the heart-wall of the patient and then aligned and drawn towards each other to be positioned in recessed areas along the periphery of the stabilizer. When the tapes are located in the recessed areas, the tapes are then drawn away from each other to be positioned in the desired retaining slots on the holding members. The surgeon can include additional tissue around the blood vessel as the tapes are tightened so that the blood vessel is compressed by the adjacent tissue rather than being directly constricted by the tapes. Additionally, the surgeon can position the tapes at a relatively wide angle of approach when the tapes are threaded around the outer surface of the stabilizer so that more tissue is positioned between the tapes and the blood vessel. The route used by the surgeon varies depending on the depth of the desired blood vessel and the surgeon's preferred approach to performing the anastomosis. The combination of the stabilizer and the tapes provides a system that does not require the significant compression or upward traction as required by the prior devices to obtain a suitable surgical site.

Similarly, a further feature of the present invention includes the provision of a lower profile for the present invention to provide a reduced likelihood that the stabilizer might interfere with the placement of the tapes or performing the graft procedure. This lower profile form is accomplished by providing a surface portion that is generally flat with no upstanding ridges or circumferential ridges. As shown and described below, this feature is located between the distal and proximal tape holder elements.

In a further preferred embodiment, the stabilizer may also include a plurality of tabs extending downwardly from the bottom surface of the stabilizer along the ends of the aperture area. The use of the tabs in combination with the tapes causes the tissue in the aperture area to be raised upwardly a small amount to expose the portion of the blood vessel that is to be the subject of the anastomosis. Additionally, a tab may be oriented to preferably extend downwardly from the proximal end of the aperture area to create contact surfaces along the ends sides of desired surgical site to further restrict the flow of blood through the blood vessel during the procedure while the distal end of the aperture also includes a downwardly extending tab to obstruct the back flow of blood through the target blood vessel. Alternately, the distal portion of the stabilizer may include a pair of spaced apart tabs to assist capturing the tissue adjacent to the distal end of the aperture area.

When the present invention is used in a coronary artery bypass procedure, the stabilizer is positioned in a desired position along the myocardial surface of the patient. One or more tapes, for example, silastic tape (i.e. a silicon elastomer) or suture thread, are passed through the myocardium at a location adjacent to the intended artery graft site with a blunt needle. The stabilizer is then loosely positioned in the desired relative position along the myocardium of the patient. Both ends of each tape are connected to the stabilizer platform with sufficient tension to draw the tissue into contact with the bottom surface of the platform and to occlude blood flow on the upstream or distal side of the operative site. The stabilizer is then securely positioned in the desired relative position along the myocardium of the patient. The tape compresses the artery and surrounding tissue against the bottom surface of the platform while the artery graft site is held in a fixed position relative to the aperture area. The coronary artery is opened longitudinally and the end of the mammary artery or other blood vessel is sewn to the graft opening with multiple fine sutures. Once the graft is completed, the distal tapes may be released and the end portion of the stabilizer may be removed to open the aperture area. The proximal tape may then be released to restore blood flow to the blood vessel and the anastomosis is then inspected for hemostasis and other defects. The anastomosis is then readily removable from the end of the stabilizer through the open end of the aperture area. Alternately, the stabilizer may be separated prior to the release of the tapes.

Figure 1:
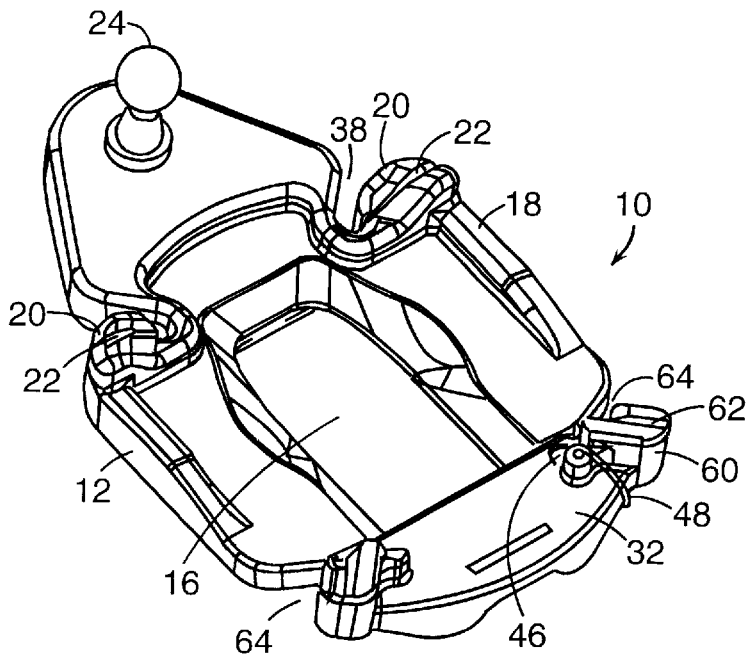
FIG. 1 is a top perspective view of a stabilizer in accordance with the preferred embodiment of the invention.
Figure 2:
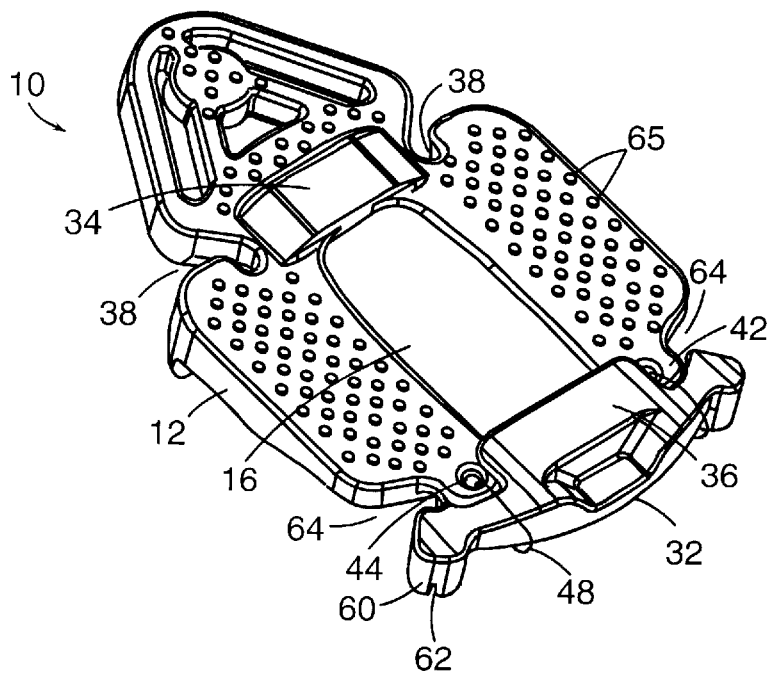
FIG. 2 is a bottom perspective view of the stabilizer in accordance with the preferred embodiment of the invention.
Figure 3:
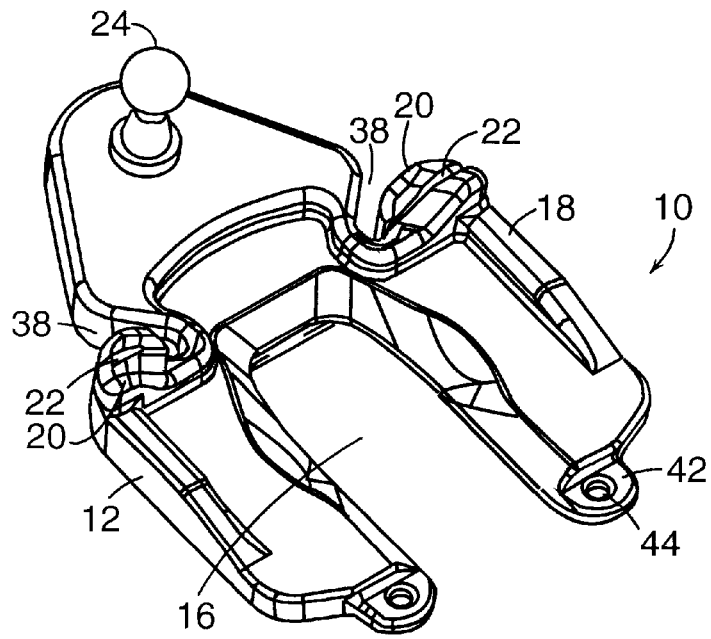
FIG. 3 is a top perspective view of the stabilizer in accordance with the preferred embodiment of the invention having the end portion removed.
Figure 4:
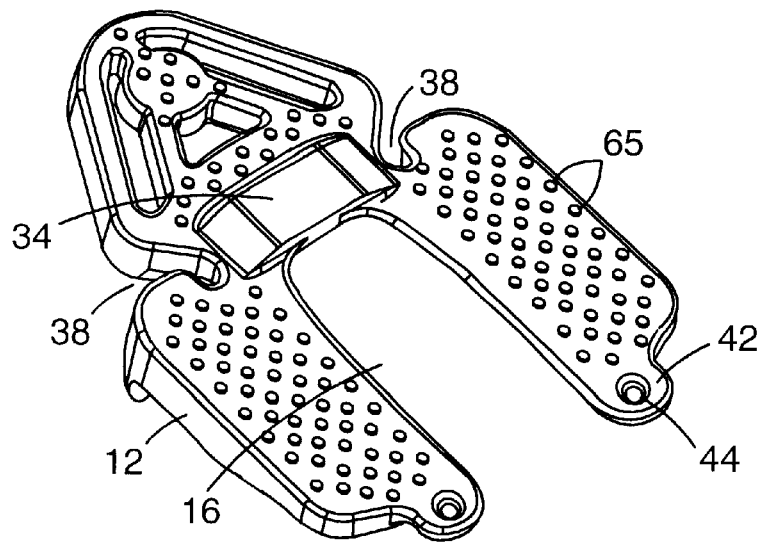
FIG. 4 is a bottom perspective view of the stabilizer in accordance with the preferred embodiment of the invention having the end portion removed.
Figure 5:
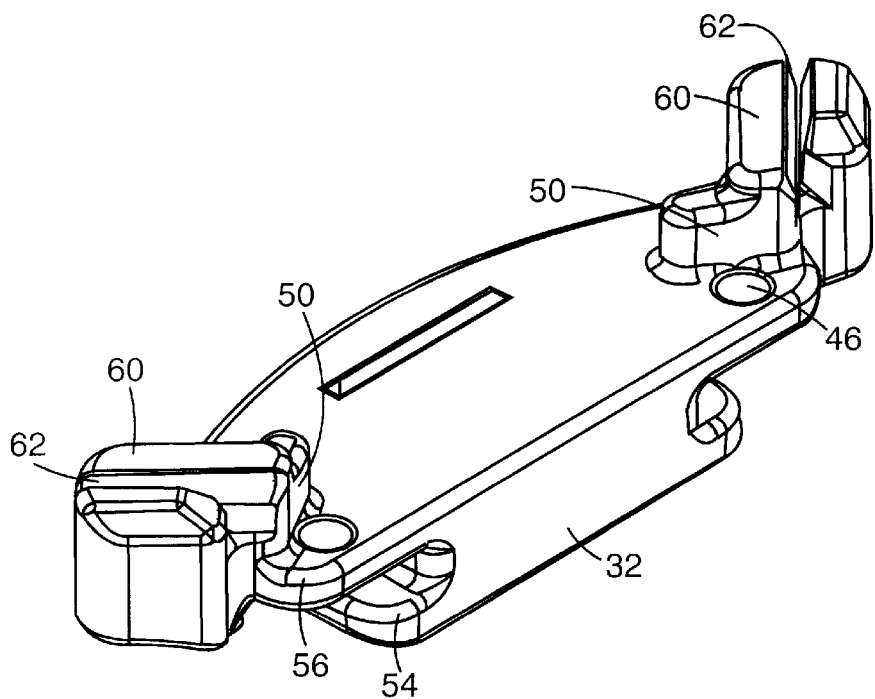
FIG. 5 is a top perspective view of the end portion of the stabilizer in accordance with the preferred embodiment of the invention.
Figure 6:
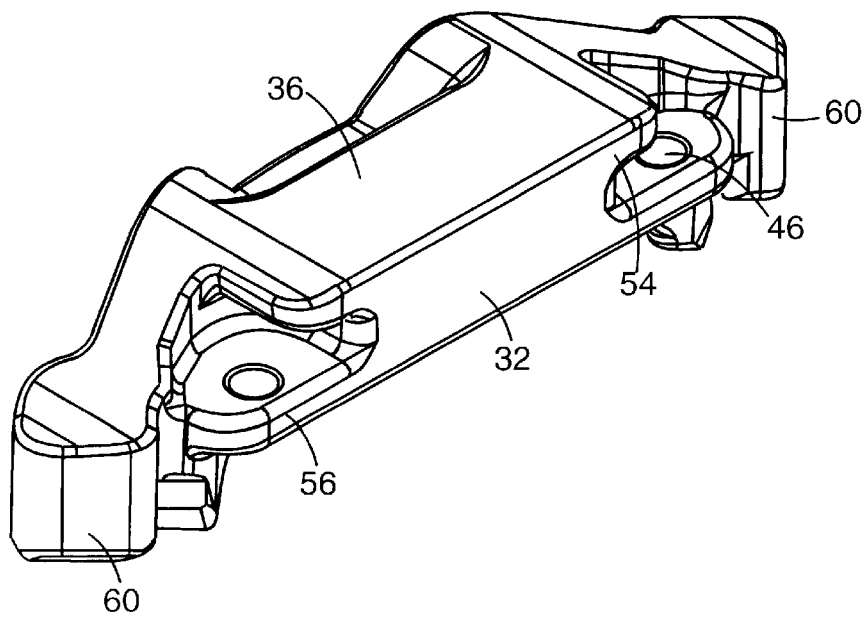
FIG. 6 is a bottom perspective view of the end portion of the stabilizer in accordance with the preferred embodiment of the invention.
Figure 7:
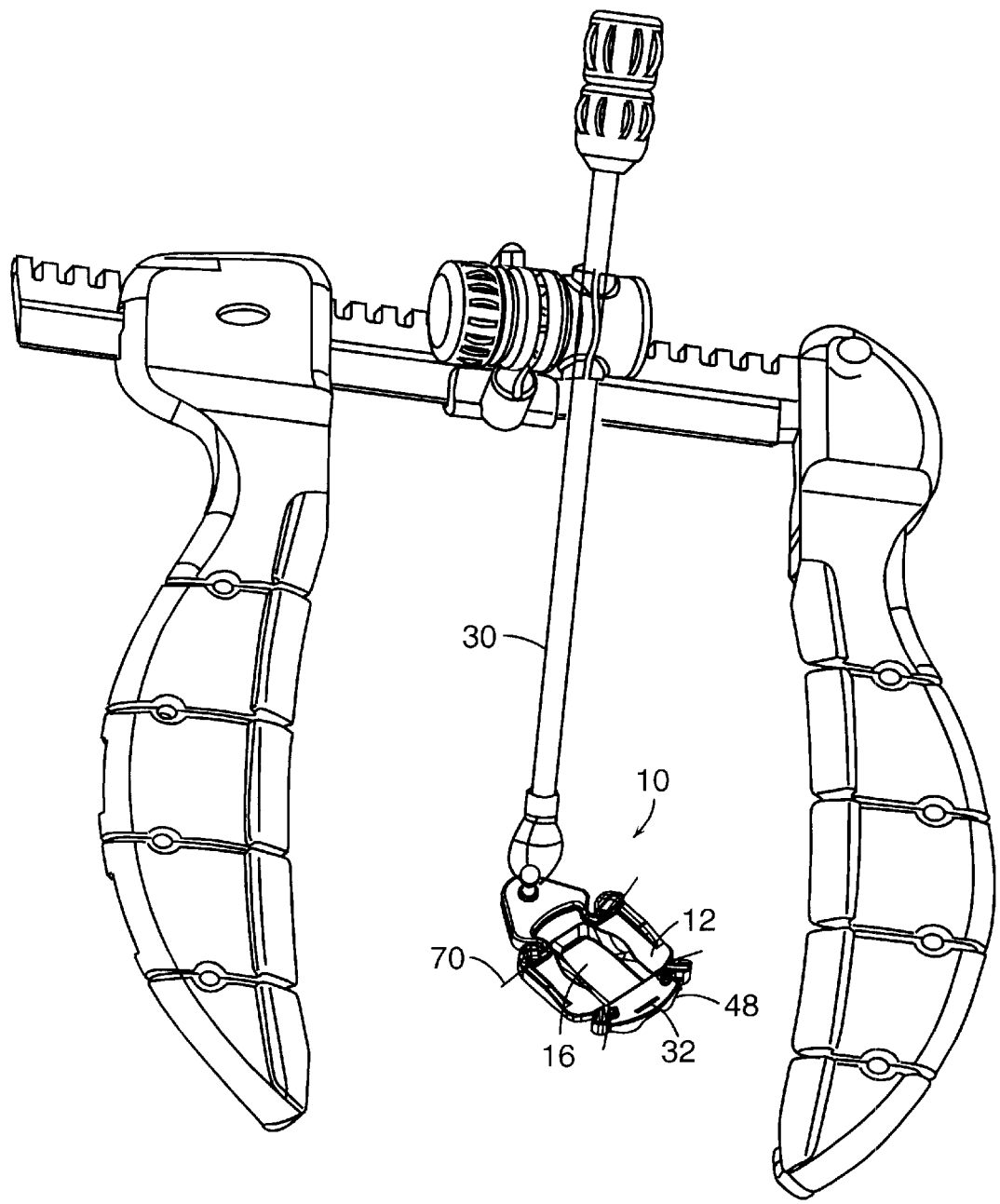
FIG. 7 is a perspective view of a chest retractor and handle supporting a stabilizer and schematically illustrating the desired position on a blood vessel in accordance with the invention.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A preferred embodiment of the invention is illustrated in connection with FIGS. 1–8. A stabilizer 10 includes a platform or base 12 having an aperture area 16 that is closed by a removable end portion 32. The aperture area 16 is positioned in use to expose tissue at a surgical site. The stabilizer 10 can be made with nearly any material, including a metal or a molded plastic material. The stabilizer 10 can be disposable after one procedure or sterilized after each use. A handle 30 or articulating arm can be permanently attached to a connector 24 on the base 12 of the stabilizer 10, or as described below in connection with other preferred embodiments, can be detachable. As used herein, the term proximal is used to generally describe the portion of the stabilizer 10 near the connector 24 and the term distal is used to describe the portion of the stabilizer 10 spaced apart from the connector 24.

In a preferred embodiment of the invention, the platform has a substantially ovoid, rectangular or elongate shape with each side having a width in the range between about 0.75 cm. and 2 cm. and a length in the range of about 3.0 cm and 6 cm. Thus the surface area of the platform is between about 2.25 cm$^2$ and 12 cm$^2$, preferably between about 5 cm$^2$ and 10 cm$^2$. This size fits readily in the incision in the chest of the patient either during typical open chest surgery or less or minimally invasive surgery and can be positioned along nearly any surface of the heart. The upper surface of the base 12 of the stabilizer 10 preferably includes a raised lip area 18 surrounding the proximal sides of the stabilizer 10 and a pair of spaced apart and raised upstanding holding members 20 having slots 22 associated therewith. A connector 24, such as a ball member, is positioned along the proximal end of the base 12 of the stabilizer 10 and is spaced apart proximally from the aperture area 16. In the preferred form of this invention, the connector 24 is positioned adjacent to the proximal end and is releasably attachable to a handle member 30. The remaining distal side of the stabilizer 10 includes a releasable end portion 32 to enclose the aperture area 16.

Additionally, the base 12 preferably includes a pair of spaced apart recessed areas 38 on the sides thereof. The pair of recessed areas 38 preferably extend inwardly from the periphery of the base 12 and are aligned generally adjacent to the holding members 20 and adjacent to the proximal end of the aperture area 16. As shown, the pair of the recessed areas 38 preferably decreases in width and curve a small amount inwardly from the periphery of the stabilizer to allow the tapes 70 to be threaded therein. The tapes 70, as used with the stabilizer 10 of the present invention may be made of nearly any material such as suture, thread or SILASTIC, stretchable material. The recessed areas 38 assist in retaining the tapes in the desired position prior to threading the tapes into the holding members 20 and also assist in holding the tapes out of the aperture area so as to not interfere with the surgical procedure 16. In this embodiment, the user may pull the tapes toward the respective ends of the stabilizer to diagonally thread the tapes into the recessed areas 38. Once the tapes are received in the recessed areas, they may be pulled outwardly and downwardly into the holder members 20 and slots 22. The width of the pairs of recessed areas 38 are sized to removably receive the connecting tapes 70 therein. The inner surface of the recessed areas also preferably assist in aligning the tapes 70 with the holder members 20 and slots 22 located along the exterior surface of the stabilizer 10 and the distal and proximal ends of the aperture area 16.

The size of the aperture area 16 can be in the range of about 0.1 and 2 cm. in width and about 0.5 and 5 mm in length. The aperture area 16 can be of various configurations including, wider in the center and narrower at the ends adjacent to the connector 24 and the end portion 32 as shown in the preferred form of the present invention. In the preferred form of the present invention, the sides of the aperture area 16 are slightly curved to provide a wider area at the center of the aperture area than at the ends of the aperture area to assist in framing the surgical site for the surgeon as the tissue is exposed and to provide a slightly wider working area. As shown, the aperture area 16 of the stabilizer is formed to include a proximal side and lateral sides that are formed as part of the base 12 and the distal side that is formed by the removable end portion 32. As referenced above, the combined use of the tapes 70 and the holding members 20 cause the tissue to extend upwardly a small amount into the aperture area to be captured therein during the surgical procedure.

The distal end portion of the base includes a contact area 42 extending along each side of the aperture area 16. The contact area 42 includes a pair of generally flat, extending surfaces thereon that are sized for the receipt of the end portion 32 thereon. The end portion 32 of the stabilizer 10 is sized to be frictionally received on the distal end of the base 12 and to close the distal end of the aperture area 16. Additionally, a suture hole 44 is located along each side of the contact area to receive a suture 48 that is threaded through a similar suture hole 46 located on the end portion 32. The suture holes 44 and 46 allow the end portion 32 to be fixedly attached to the base 12 via a suture 48 that is threaded through the suture holes 44 and 46. The use of the suture 48 and suture holes reduce the likelihood that the end portion 32 may become disengaged from the base prematurely during the surgical procedure. Once the anastomosis is completed, the surgeon may cut one or both of the sutures 48 using a blade or other instrument. The sides of the end portion 32 also include upper and lower extensions, 54 and 56 that are sized and positioned to extend inwardly and frictionally receive the contact area 42 from the base 12 therein so that the end portion is frictionally retained on the base even after the suture 48 is cut by the surgeon. Although the end portion is preferably retained on the base 12 using the suture 48, it is anticipated that various other mechanisms may be used, such as clips, adhesives or other temporary retaining members.

As shown, the end portion 32 also includes a pair of upstanding holder members 60 and slots 62 located along the proximal exterior surface thereof. Additionally, the outer surface of the proximal end of the base member and the distal side of the holder members 60 on the end portion 32 also form recessed areas 64 adjacent thereto. As with the recessed areas and holder members described above on the distal end of the aperture area, the recessed areas 64, holder members 60 and the slots 62 are formed on the end portion 32 to allow the tape 70 to be threaded inwardly into the recessed areas 64 and then pulled outwardly and downwardly into the holder members 60 and slots 62. The end portion also preferably includes a pair of raised lip areas 50 adjacent to the suture holes to allow the surgeon to cut the suture adjacent to the raised lip areas 50 to reduce the likelihood that the graft might be damaged during the removal of the end portion 32. The end portion 32 may also preferably includes a radio-opaque marker thereon or may include radio-opaque materials therein to enable the surgeon to located the end portion 32 of the stabilizer in the event that the end portion is accidentally separated from the base 12 during the procedure.

The bottom surface 14 of the stabilizer 10 includes a proximal tab member 34 and the end portion 32 includes a similar distal tab member 36 extending downwardly therefrom. The tab members 34 and 36 are preferably shaped as elongate tapered members that taper downwardly and extend from the bottom surface 14 of the stabilizer 10 along the proximal and distal ends of the aperture area 16. The tab members 34 and 36 are also preferably longer than it is wide and are aligned generally perpendicular to the lengthwise dimension proximal side of the aperture area 16 and the intended alignment of the blood vessel. In use, tab member 34 and 36 are positioned to reduce blood flow from the blood vessel into the surgical site formed by the aperture area 16. Alternately, either of the tab members 34 or 36 may be formed as a pair of spaced apart tab members (not shown) to apply pressure to the tissue adjacent to the blood vessel along the one or both ends of the aperture area. In the preferred form of the present invention, the tab members 34 and 36 are formed to extend at least partially from the bottom surface of the base member and the end portion 32 such that the tab members 34 and 36 apply pressure to the blood vessel. A plurality of relatively small spaced apart gripping surfaces 65 are also located on the bottom surface 14 of the base to assist in maintaining contact between the tissue of the patient and the stabilizer 10. Alternately, the bottom surface 14 of the base 12 that is in contact with the myocardium may be roughened, abraded or include adhesives thereon to frictionally engage the heart wall around the artery and thereby locally restrict heart motion around the surgical site.

In the preferred embodiment of the present invention, the stabilizer 10 can have a connector 24, such as a ball member from a ball and socket connection, or a similar handle attachment mechanism so that the user can attach a handle 30 to the stabilizer 10 to provide convenient access to the aperture area 16 and facilitate immobilization of the tissue surrounding the artery. The connector 24 can be located along the proximal end portion of the base and is positioned between or adjacent to the tapes relative to the aperture area and also preferably extends above the top surface of the stabilizer 10. This structure exerts little downward force or upward force on the heart on the artery while immobilizing the tissue at the surgical site. Also the anterior-posterior compression of the artery avoids trauma to the artery due to circumferential compression. As shown, the tapes 70 under the bottom surface of the tabs 34 and 36 lifts the artery to form an occlusion by compressing the artery between the tissue captured by the tape and the bottom surface of the stabilizer 10.

A preferred embodiment of the invention can be used at a surgical site to perform an anastomosis during a bypass procedure. In this particular procedure for a coronary graft without cardiopulmonary bypass, a proximal portion of the LIMA is dissected from the chest wall to expose an end to be grafted onto a grafting site on the coronary artery. Alternately, the saphenous vein may be harvested from a leg of the patient for use as the bypass conduit. The exposed surface of heart is undergoing substantial three-dimensional movement during the procedure as the heart is allowed to continue beating in the usual manner. Blood flow in the vessel can be occluded with a clamp. In this example, a connector such as a suture, thread, cord or silastic tape 70 is threaded through myocardium surface under the coronary artery on opposite sides of the desired grafting site. The stabilizer 10 preferably serves to immobilize the grafting site using the platform portion of the stabilizer and the connecting tape 70 which is stretched and attached to a holder member 20 including one or more slots 22 in the peripheral edge of base 12. As described in greater detail below, the ends of the tapes 70 can be manually positioned in the slots 22 to allow the user to adjust the tension in the tapes or threads. The stabilizer 10 is also preferably secured at the site by attaching the stabilizer to the handle 30 or arm and to a chest retractor or other implement. Therefore, the grafting site preferably undergoes a minimal amount of movement relative to the stabilizer in any direction during the surgical procedure.

Figure 9:
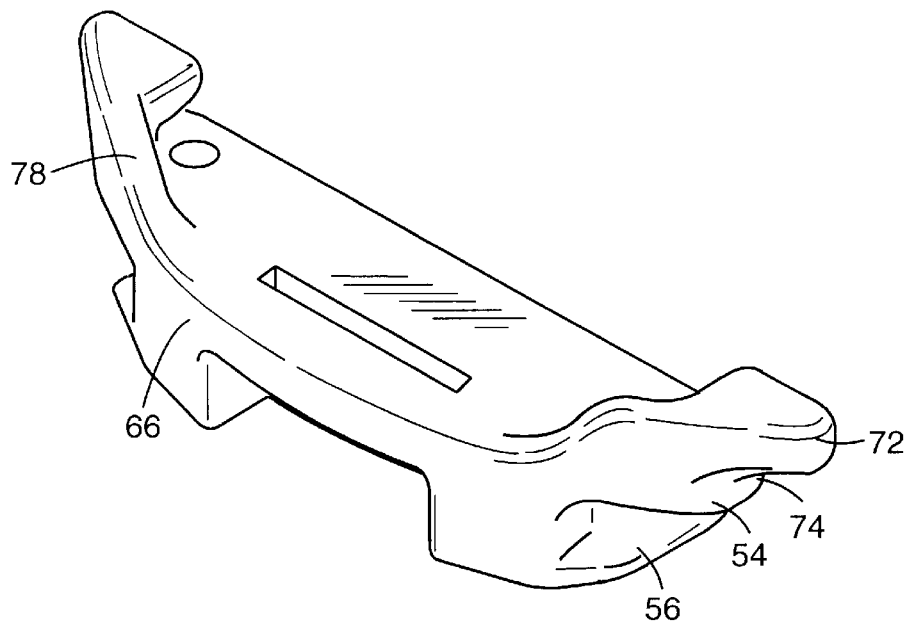
FIG. 9 is a top perspective view of the end portion of the stabilizer in accordance with an alternate form of the present invention.

In the preferred procedure as diagrammatically illustrated in FIG. 9, the tapes 70 are inserted in the myocardium with a blunt needle approximately 1–2 cm apart. The tapes are inserted into the myocardium beneath the desired coronary artery a sufficient distance to include a portion of the tissue adjacent to the artery so that the artery is not excessively constricted during the following procedure. The stabilizer 10 is initially positioned loosely adjacent to the desired surgical site. Once the tapes 70 are pulled through the tissue, the tapes are threaded into the respective recessed areas 38 and 64 on the exterior of the stabilizer 10. The stabilizer is then moved into the desired position and the tapes 70 are tensioned through the recessed areas 38 and 64 to draw tissue against the tab members 34 and 64 up into the aperture area 16. The tensioned tapes are then connected to the slots 22 of the on the holding members 20 of the stabilizer 10 to compress the artery and occlude blood flow distally or upstream of the grafting site and proximally or down stream of the grafting site. The stabilizer 10 is then locked into the desired positioned adjacent to the desired surgical site to assist in the retention of the desired tissue in the aperture area 16 by locking the stabilizer 10 relative to the handle 30 and relative to the chest retractor. The tension in the tapes can be adjusted during the procedure to minimize blood loss at the site and to temporarily verify the flow of blood through the grafted blood vessel.

After the procedure is complete, the stabilizer 10 may be easily removed from the surgical site. In the preferred embodiment, the suture 48 may be cut and the end portion 32 may be removed from the base 12. The tapes 70 may then be released from the distal and proximal slots. Once the end portion 32 is removed and the tapes are released therefrom, the base 12 includes an open ended aperture area 16 to enable the completed anastomosis to be removed therefrom. This is accomplished by releasing the stabilizer from the locked position relative to the handle 30 and/or the chest retractor and moving the base 12 of the stabilizer relative to the anastomosis. Thereafter, the stabilizer may be reused on another location of the heart by the surgeon. The stabilizer 10 may be reused on the same patient by retying a portion of suture through the suture holes 44 and 46. Alternately, a new stabilizer 10 may be quickly placed on the handle 30. The stabilizer 10 may then be moved to the next desired location on the heart of the patient and the steps set forth above may be repeated.

Figure 10:
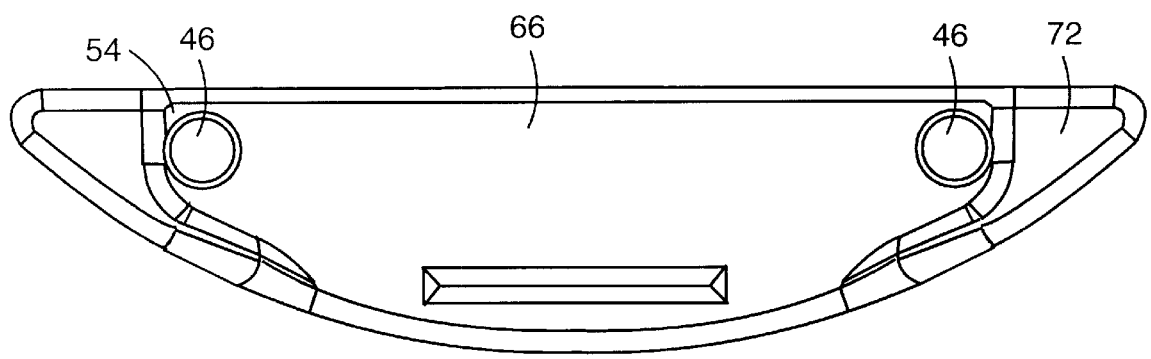
FIG. 10 is a top view of the end portion of the stabilizer in accordance with an alternate form of the present invention.
Figure 12:
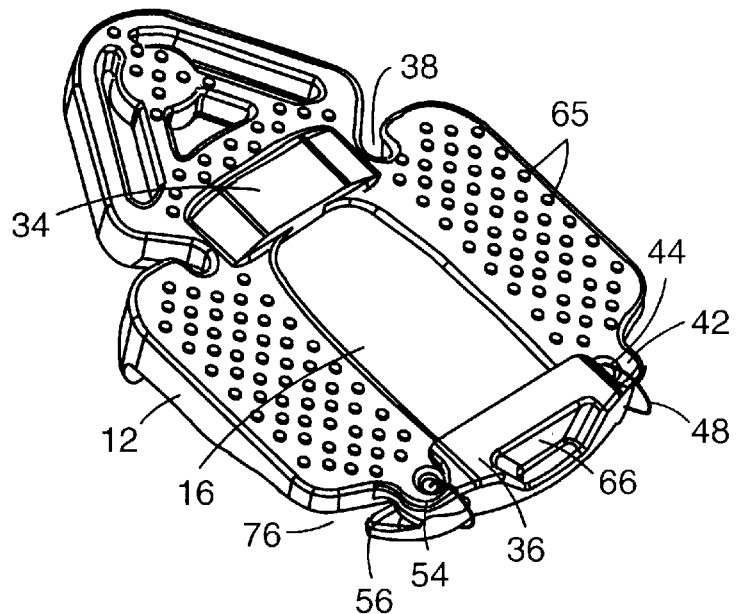
FIG. 12 is a bottom perspective view of the stabilizer in accordance with the alternate embodiment of the present invention.
Figure 11:
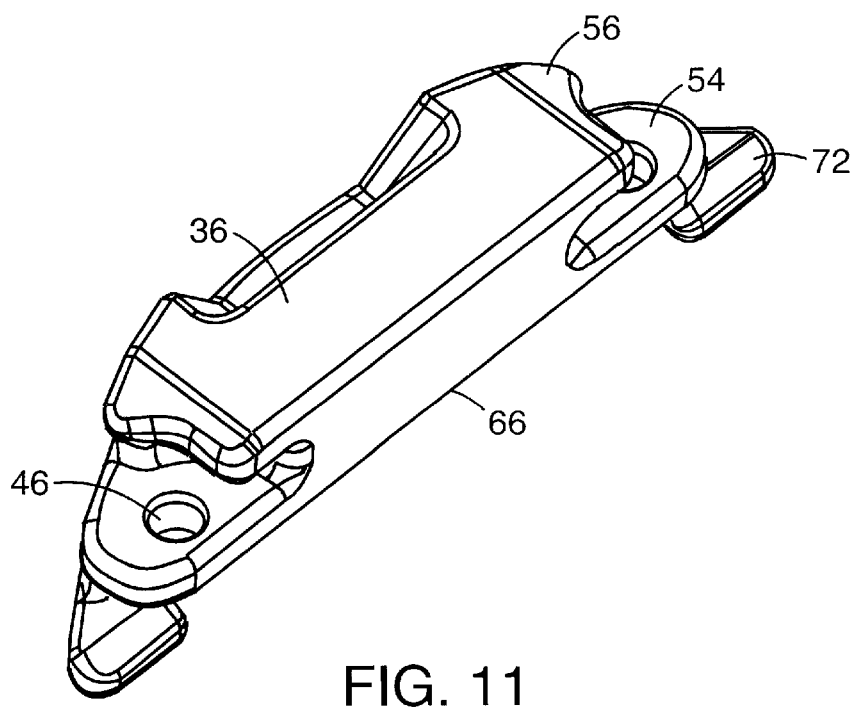
FIG. 11 is a bottom perspective view of the end portion of the stabilizer in accordance with the preferred embodiment of the invention.

FIGS. 10–12 are illustrative of an alternate form of the present invention wherein a modified end portion 66 is provided on the base 12 as described above. The end portion 66 of this embodiment includes a stabilizer 10 that is sized to be frictionally received on the distal end of the base 12 and to close the distal end of the aperture area 16. The sides of the end portion 66 also include upper and lower extensions, 54 and 56 that are sized and positioned to extend inwardly and frictionally receive the contact area 42 from the base 12 therein so that the end portion is frictionally retained on the base even after the suture 48 is cut by the surgeon. The extensions, 54 and 56, are also sized and positioned to receive the contact area 42 from the base 12 thereon so that the end portion is aligned with the distal end of the base when the suture 48 is passed through the suture holes 44 and 46. Although the end portion of this embodiment is preferably retained on the base 12 using the suture 48, it is anticipated that various other mechanisms may be used, such as clips, adhesives or other temporary retaining members. As shown, the end portion 66 also includes a pair of laterally extending holder members 72 and slots 74 located along the proximal exterior surface thereof. Additionally, the outer surface of the distal end of the base member and the proximal side of the holder members 72 on the end portion 66 also form recessed areas 76 adjacent thereto. The recessed areas 76, holder members 72 and the slots 74 formed on the end portion 32 of the alternate embodiment, allow the tape 70 to be threaded inwardly into the recessed areas 76 and then pulled outwardly and laterally into the holder members 72 and slots 74. The end portion also preferably includes a pair of raised areas 78 adjacent to the suture holes to allow the surgeon to cut the suture adjacent to the raised areas 78 to reduce the likelihood that the graft might be damaged during the removal of the end portion 32. In this embodiment, the holder members 72 may also be used similar to a cleat to allow the tapes 70 to be tightened around the holder members 72 as they are pulled into the slots 74

Although the use of the stabilizer has been described in connection with a particular bypass procedure, it can also be used in other procedures such as bypass operations involving the diagonal, right or other coronary artery or in surgery for other organs or tissues where movement at the site can interfere with the procedure.

Alternative embodiments involve opening of the chest and positioning the stabilizer at any exposed site on the heart wall or surrounding areas to immobilize the operative site. The stabilizer serves to isolate the site and limits motion at the surgical site due to respiratory movement of the lungs or the pumping motion of the heart.

Figure 8:
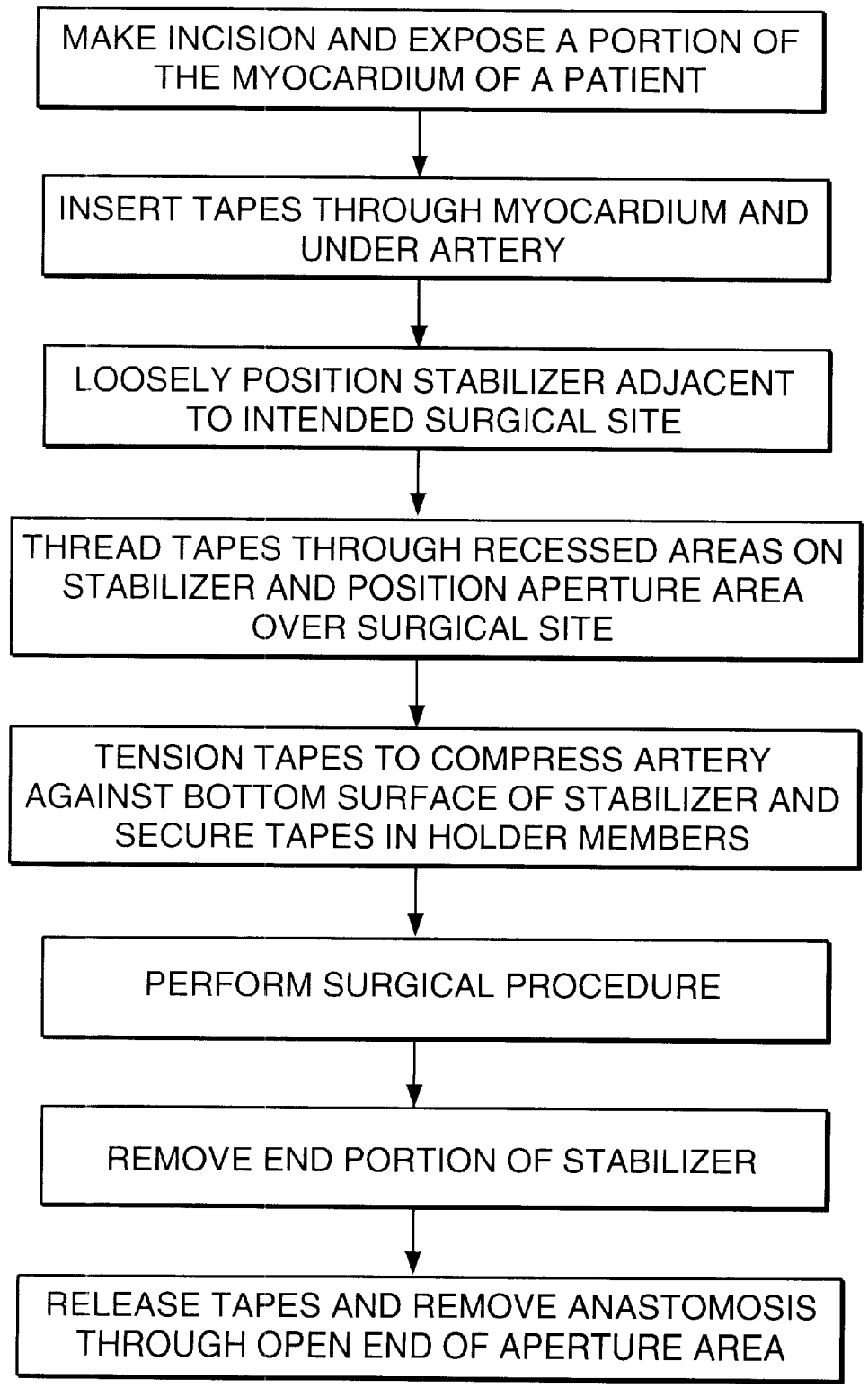
FIG. 8 is a schematic diagram illustrating a surgical procedure in accordance with the preferred form of the present invention.

In the preferred embodiment, a retractor system or frame manufactured by Genzyme Biosurgery is illustrated in FIG. 8 to support a stabilizer in accordance with the invention.

While this invention has been particularly shown and described with references to preferred embodiments thereof, it will be understood by those skilled in the art that various changes in form and details may be made therein without departing from the spirit and scope of the invention as set forth in the appended claims.

What is claimed:

1. A surgical device for a coronary bypass procedure comprising:
   a generally rigid stabilizer having a platform area having a length dimension that is greater than the width dimension and including a base portion and a removable end portion wherein the stabilizer includes an aperture area defining an operative site wherein the aperture area includes a proximal end portion, a pair of sides and a distal end portion and the removable end portion includes a pair of raised holding members adjacent to the aperture area and the removable end portion is removably retained on the base portion adjacent to the distal end portion of the aperture area.

2. The surgical retractor of claim 1, having raised sidewall elements disposed along the longitudinal dimension of the proximal end portion of the stabilizer.

3. The surgical retractor of claim 2, wherein the raised sidewall elements have at least one raised holding member thereon to frictionally grip an end of a flexible connector.

4. The surgical retractor of claim 1, further including a flexible connector wherein the flexible connector is adapted to extend through the tissue of a patient and the flexible connector is retained in the pair of raised holding members on the removable end portion of the stabilizer.

5. The surgical retractor of claim 1, wherein the stabilizer includes at least one tab member adjacent to the aperture area and the tab member extends downwardly from the bottom surface of the stabilizer and is sized to compressingly contact the tissue of a patient.

6. The surgical retractor of claim 1, wherein the stabilizer has a plurality of recessed areas extending from the periphery thereof and the recessed areas are adapted to receive a flexible connector therein and under the stabilizer such that the connector retains tissue at the surgical site within the aperture area.

7. The surgical retractor of claim 1, further including one or more flexible connectors wherein the flexible connectors extend beneath the stabilizer and are adapted to extend through the tissue of a patient to draw the tissue of a patient into the aperture area and wherein the flexible connectors are releasably connected to the raised holding members of the stabilizer.

8. The surgical retractor of claim 1, wherein the stabilizer further includes a raised connector thereon and the raised connector is sized to receive a handle member connected thereto.

9. The surgical retractor of claim 1, wherein the removable end portion of the stabilizer is frictionally received on the base portion of the stabilizer.

10. The surgical retractor of claim 1 wherein said removable end portion is retained on the base by a connecting member that is severable to release the removable end portion from the base portion of the stabilizer.

11. A surgical device for a coronary bypass procedure comprising:
    a generally rigid stabilizer having a top surface and a bottom surface and platform area having a length dimension that is greater than the width dimension and said platform area encloses an aperture area defining an operative site wherein the aperture area includes a proximal end portion, a pair of sides and a distal end portion and a removable end portion is removable from the platform area and said removable end portion includes a downwardly extending tab member extending from the bottom surface of the removable end portion and the tab member is oriented generally perpendicular to the sides of the aperture area.

12. The surgical retractor of claim 11, having raised sidewall elements disposed along the periphery of the longitudinal dimension of the top surface of the proximal end portion of the stabilizer.

13. The surgical retractor of claim 12, wherein the raised sidewall elements of the top surface include at least one raised holding member associated therewith to frictionally grip an end of a flexible connector.

14. The surgical retractor of claim 11, further including a flexible connector wherein the flexible connector is adapted to extend through the tissue of a patient and the proximal end portion of the top surface of the stabilizer includes a pair of raised holding members and the flexible connector is retained in the raised holding members on the stabilizer.

15. The surgical retractor of claim 11, wherein the stabilizer includes said removable end portion adjacent to the distal end portion of the aperture area and said removable end portion includes a pair of raised holding members and is releasable from the platform area to allow tissue positioned in the aperture area to be removed therethrough.

16. The surgical retractor of claim 11, wherein the stabilizer has a plurality of recessed areas extending from the periphery thereof and the recessed areas are adapted to receive a flexible connector therein and under the stabilizer such that the connectors position tissue at the surgical site within the aperture area.

17. The surgical retractor of claim 11, further including one or more flexible connectors wherein the flexible connectors extend beneath the stabilizer and are adapted to extend through the tissue of a patient to draw the tissue of a patient into the aperture area and wherein the flexible connectors are releasably connected to a plurality of raised holding members on the top surface of the removable end portion of the stabilizer.

18. The surgical retractor of claim 11, wherein the stabilizer further includes a raised connector thereon and the raised connector is sized to receive a handle member connected thereto.

19. The surgical retractor of claim 11, wherein the platform area includes a base portion and the removable end portion and the removable end portion of the stabilizer is frictionally received on the base of the stabilizer to enclose distal end portion of the aperture area.

20. The surgical retractor of claim 19 wherein said removable end portion is retained on the base by a connecting member that is severable to release removably the end portion from the base of the stabilizer.

21. A surgical retractor comprising:
  a rigid retaining element having a generally elongate platform section wherein said platform section has a length dimension that is larger than the width dimension and wherein said lengthwise dimension is formed by a pair of laterally extending members and said width dimension and said laterally extending members form an enclosed aperture area having a proximal end portion, a distal end portion and a pair of sides and wherein said aperture area is sized to allow the attachment of a graft at a surgical site therein;
  a plurality of recessed areas extending inwardly from the periphery of the platform section;
  a pair of raised holding members on said distal end portion and wherein said raised holding members are adjacent to said recessed areas.

22. The surgical retractor of claim 21 further including a raised connector adjacent to said proximal end portion and said raised connector is sized for attachment to a handle member to allow for the application of a tissue restraining force against the surgical site by said stabilizer.

23. The surgical retractor of claim 21 further including a flexible connector removably attached to said raised holding members wherein said flexible connector is interconnected with said stabilizer to allow for the application of a tissue restraining force against the surgical site adjacent to said aperture area.

24. The surgical retractor of claim 21 further including a pair of tab members extending downwardly from a bottom surface of the stabilizer wherein the tab members are aligned with the proximal end portion and distal end portion of the aperture area.

25. The surgical retractor of claim 21 further including a tab member extending downwardly from a bottom surface of the platform section wherein the tab member is aligned with the proximal end portion of the aperture area.

26. A method of stabilizing a surgical site during surgery comprising the steps of:
  positioning a stabilizer at the surgical site wherein the stabilizer is formed having a width dimension and a lengthwise dimension and wherein the lengthwise dimension is formed of a pair of laterally extending members and said width dimension and said laterally extending members form an aperture area therebetween and further including a removable end portion thereon and wherein the aperture area is sized to allow the formation of a graft therein;
  threading a flexible connector through tissue surrounding the surgical site and removably attaching the flexible connector to the removable end portion of the stabilizer to stabilize the tissue adjacent to the surgical site with respect to the stabilizer;
  performing a surgical procedure including grafting a first blood vessel to a second blood vessel;
  releasing the flexible connector from the end portion and removing the end portion of the stabilizer; and
  removing the stabilizer from around the graft performed in the aperture area.

27. The method of claim 26 further including the step of releasably attaching the flexible connector to a plurality of raised holding members on the stabilizer to apply an upwardly directed force to the tissue adjacent to the surgical site.

28. The method of claim 27 further including the step threading the flexible connector through a plurality of recessed areas along the periphery of the stabilizer and attaching the flexible connector to raised holding members on the stabilizer to apply an upwardly directed force to the tissue adjacent to the surgical site.

29. A method of stabilizing a surgical site during surgery comprising the steps of:
  positioning a stabilizer at the surgical site wherein the stabilizer is formed having a base portion and an end portion and a width dimension and a lengthwise dimension and wherein the lengthwise dimension is formed of a pair of laterally extending members and said width dimension and said laterally extending members form an aperture area therebetween along three sides of the surgical site and wherein the end portion is removable and extends along the remaining side of the aperture area;
  attaching a handle member to the stabilizer to stabilize the tissue adjacent to the aperture area with respect to the stabilizer and attaching a flexible connector to a portion of the stabilizer:
  performing a surgical grafting procedure in the aperture area; and
  releasing the flexible connector and removing the end portion from the stabilizer and removing the base from around the aperture area.

30. The method of claim 29 further including the step of threading the flexible connector through tissue adjacent to the aperture area, passing the flexible connector through recessed areas along the periphery of the stabilizer and then removably attaching the flexible connector to the stabilizer to stabilize the tissue adjacent to the surgical site with respect to the stabilizer and draw the tissue into contact with a downwardly extending tab member located on the bottom surface of the stabilizer.

* * * * *

UNITED STATES PATENT AND TRADEMARK OFFICE
CERTIFICATE OF CORRECTION

PATENT NO.     : 6,537,323 B2
DATED          : March 25, 2003
INVENTOR(S)    : Martin J. Weinstein and Quinton Farrar It is certified that error appears in the above-identified patent and that said Letters Patent is hereby corrected as shown below:

<u>Column 8,</u>
Line 34, replace "tab members 34 and 64" to -- tab members 34 and 62 --.

Signed and Sealed this

Second Day of September, 2003

JAMES E. ROGAN
*Director of the United States Patent and Trademark Office*